United States Patent
Li et al.

(10) Patent No.: US 9,770,242 B2
(45) Date of Patent: Sep. 26, 2017

(54) SURGICAL STAPLER COMPRISING SAFETY APPARATUS

(71) Applicant: B. J. ZH. F. Panther Medical Equipment Co., Ltd., Beijing (CN)

(72) Inventors: Xuejun Li, Beijing (CN); Qing Liu, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 396 days.

(21) Appl. No.: 14/561,207

(22) Filed: Dec. 4, 2014

(65) Prior Publication Data

US 2015/0083778 A1 Mar. 26, 2015

Related U.S. Application Data

(63) Continuation-in-part of application No. PCT/CN2013/000666, filed on Jun. 4, 2013.

(30) Foreign Application Priority Data

Jun. 5, 2012 (CN) .......................... 2012 1 0181763

(51) Int. Cl.
| | |
|---|---|
| *A61B 17/04* | (2006.01) |
| *A61B 17/10* | (2006.01) |
| *A61B 17/068* | (2006.01) |
| *A61B 17/115* | (2006.01) |
| *A61B 17/29* | (2006.01) |

(52) U.S. Cl.
CPC ........ *A61B 17/068* (2013.01); *A61B 17/1155* (2013.01); *A61B 2017/2946* (2013.01)

(58) Field of Classification Search
CPC ............ A61B 2019/464; A61B 17/068; A61B 17/1707; A61B 2019/5259
USPC .............................................. 227/175.1–182.1
See application file for complete search history.

(56) References Cited

U.S. PATENT DOCUMENTS

| | | | | |
|---|---|---|---|---|
| 5,005,749 A | * | 4/1991 | Aranyi ................. | A61B 17/115 227/175.1 |
| 5,474,223 A | * | 12/1995 | Viola ................... | A61B 17/072 227/175.1 |
| 7,144,405 B2 | * | 12/2006 | Vargas .................. | A61B 17/11 606/185 |
| 7,422,136 B1 | * | 9/2008 | Marczyk ........... | A61B 17/07207 227/175.1 |
| 7,721,930 B2 | * | 5/2010 | McKenna ........ | A61B 17/00491 227/175.1 |
| 7,743,960 B2 | * | 6/2010 | Whitman ......... | A61B 17/07207 227/175.1 |

(Continued)

*Primary Examiner* — Robert Long
(74) *Attorney, Agent, or Firm* — Matthias Scholl, PC; Matthias Scholl

(57) ABSTRACT

A surgical stapler including a safety apparatus, including: a stapler part, a fixed handle, a safety apparatus, a transmission assembly, a propulsion assembly, and a trigger handle. The safety apparatus includes a safety piece and a fixing block. The propulsion assembly includes an ejector sleeve. The safety apparatus is fixed on the propulsion assembly and contacts with a surface of the transmission assembly. The safety piece is disposed inside the fixing block. At least one spring is disposed inside the fixing block to ensure elasticity of the safety piece.

8 Claims, 5 Drawing Sheets

(56) References Cited

U.S. PATENT DOCUMENTS

| | | | |
|---|---|---|---|
| 8,827,134 B2* | 9/2014 | Viola | A61B 17/07207 227/176.1 |
| 2008/0275471 A1* | 11/2008 | Viola | A61B 17/128 606/142 |
| 2010/0170931 A1* | 7/2010 | Viola | A61B 17/128 227/175.1 |
| 2012/0089131 A1* | 4/2012 | Zemlok | A61B 17/07207 606/1 |
| 2016/0106418 A1* | 4/2016 | Shi | A61B 17/1155 227/175.2 |

* cited by examiner

SURGICAL STAPLER COMPRISING SAFETY APPARATUS

CROSS-REFERENCE TO RELATED APPLICATIONS

This application is a continuation-in-part of International Patent Application No. PCT/CN2013/000666 with an international filing date of Jun. 4, 2013, designating the United States, now pending, and further claims priority benefits to Chinese Patent Application No. 201210181763.1 filed Jun. 5, 2012. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a surgical stapler, and more particularly to a surgical stapler comprising a safety apparatus.

Description of the Related Art

A typical surgical stapler includes a safety mechanism that prevents inadvertent placement of the staples before the user is ready to do so. The primary problem that arises in this context is that the opening and closing of the safety apparatus is inaccurate and is adversely affected by changes in the stapling gap. Thus, either the opening range of the safety apparatus enlarges and becomes inaccurate, or the range of the safety apparatus narrows, which results in an indicator error.

In addition, because different operators vary in technique, the opening and closing of the safety apparatus and the movement smoothness are highly affected.

SUMMARY OF THE INVENTION

In view of the above-described problems, it is one objective of the invention to provide a surgical stapler comprising a safety apparatus. The safety apparatus can be triggered within a specified stroke interval.

To achieve the above objective, in accordance with one embodiment of the invention, there is provided a surgical stapler comprising a safety apparatus. The surgical stapler comprises: a stapler part, a fixed handle, a safety apparatus, a transmission assembly, a propulsion assembly, and a trigger handle. The safety apparatus comprises a safety piece and a fixing block. The propulsion assembly comprises an ejector sleeve. The safety apparatus is fixed on the propulsion assembly and contacts with a surface of the transmission assembly. The safety piece is disposed inside the fixing block. At least one spring is disposed inside the fixing block to ensure elasticity of the safety piece.

In a class of this embodiment, the transmission assembly comprises: a screw rod, a positioning connecting rod, and a gap regulator. The positioning connecting rod comprises a chute. The positioning connecting rod is in slide connection with the screw rod via a first pin. The positioning connecting rod is in flexible connection with the gap regulator via a second pin and an extension spring.

In a class of this embodiment, an end face of the safety piece is adapted to contact with the chute of the positioning connecting rod.

In a class of this embodiment, a first limit slot is disposed at one side of an inner cavity of a casing of the fixed handle.

In a class of this embodiment, an end of the safety piece contacting with the chute of the positioning connecting rod comprises an arc-shaped head.

In a class of this embodiment, the safety piece is fixed inside the fixing block via two or three compression springs.

In a class of this embodiment, the screw rod comprises a boss; and the positioning connecting rod comprises a groove having a depth smaller than a height of the boss.

In a class of this embodiment, the positioning connecting rod comprises a positioning boss.

In a class of this embodiment, a second limit slot is disposed on the gap regulator for matching with the positioning boss of the positioning connecting rod.

Advantages according to embodiments of the invention are summarized as follows:

The safety apparatus of the surgical stapler is adapted to prevent abnormal triggering of the surgical stapler thereby preventing operation failure resulting from unexpected or abnormal triggering of the surgical stapler. The surgical stapler of the invention has simple structure, convenient assembly, and safe use. The surgical stapler of the invention realizes total automatic processing and does not necessitate manual regulation, so that it is significant for the prevention of triggering error and is suitable for wide application.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a surgical stapler comprising a safety apparatus are described below. It should be noted that the following examples are intended to describe and not to limit the invention.

Figure 1:
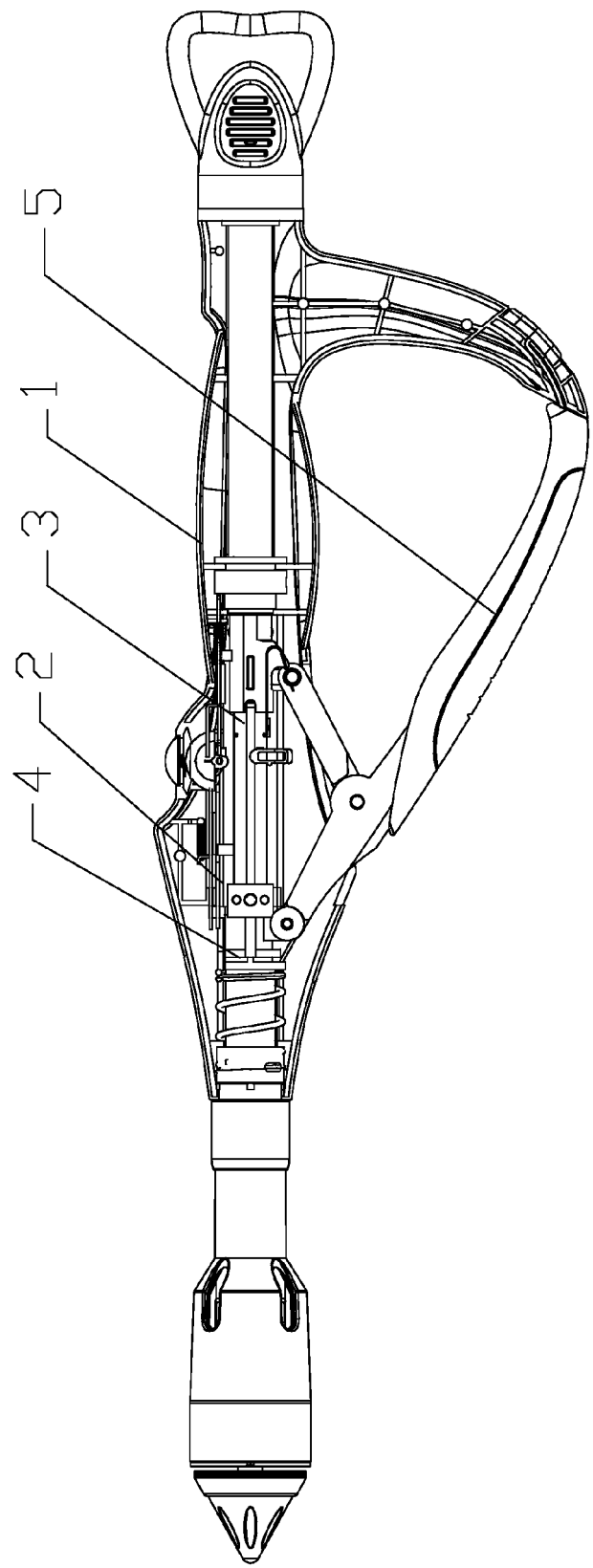
FIG. 1 is a structure diagram of a surgical stapler comprising a safety apparatus in accordance with one embodiment of the invention.
Figure 2:
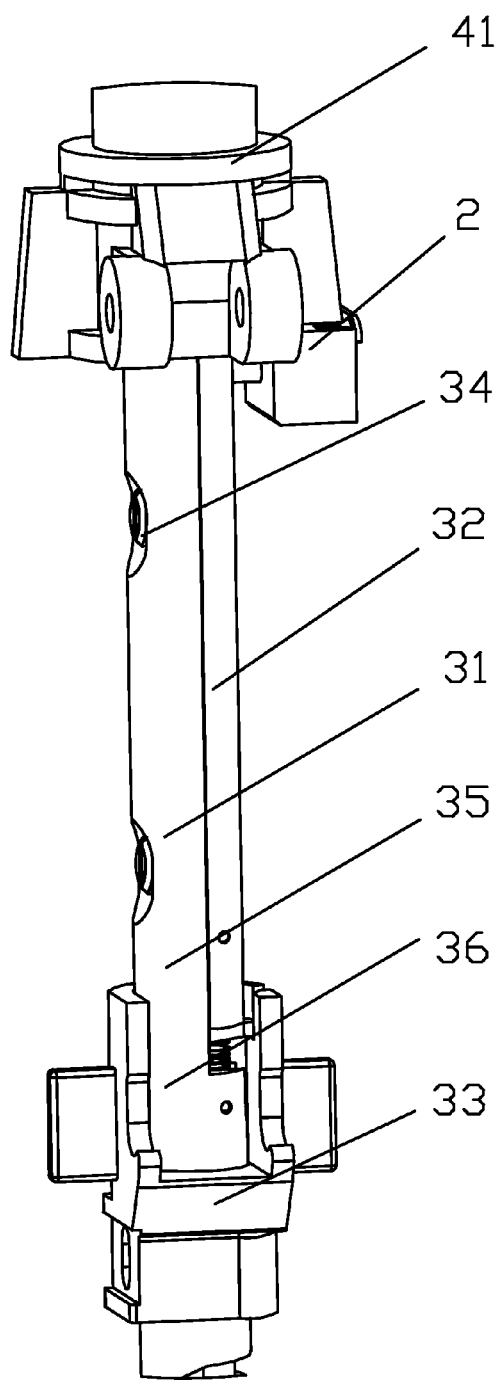
FIG. 2 is an assembly diagram of a propulsion assembly and a safety apparatus of a surgical stapler in accordance with one embodiment of the invention.
Figure 3:
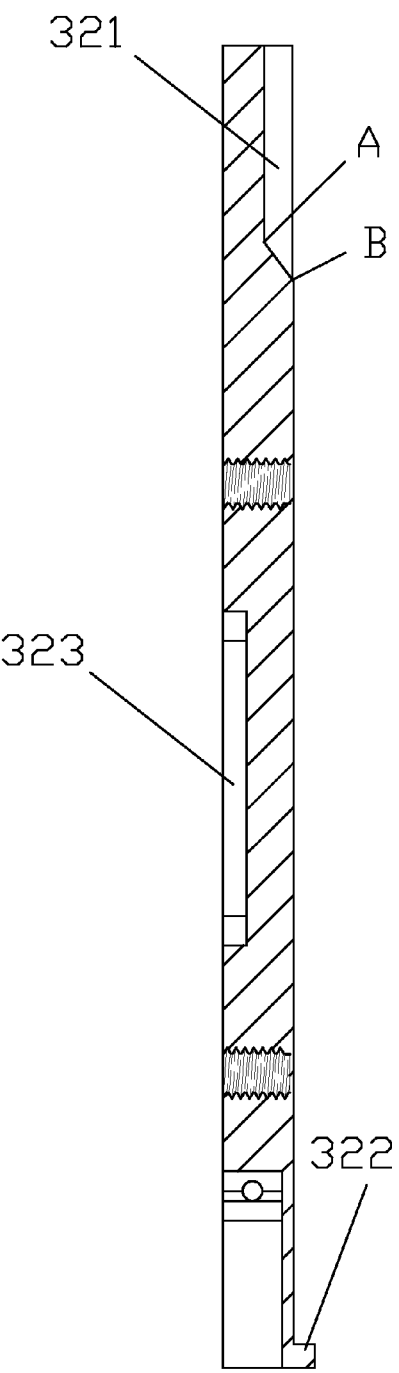
FIG. 3 is a structure diagram of a positioning connecting rod of a surgical stapler in accordance with one embodiment of the invention.
Figure 4:
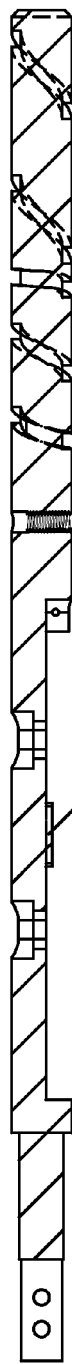
FIG. 4 is a structure diagram of a screw rod of a surgical stapler.
Figure 5:
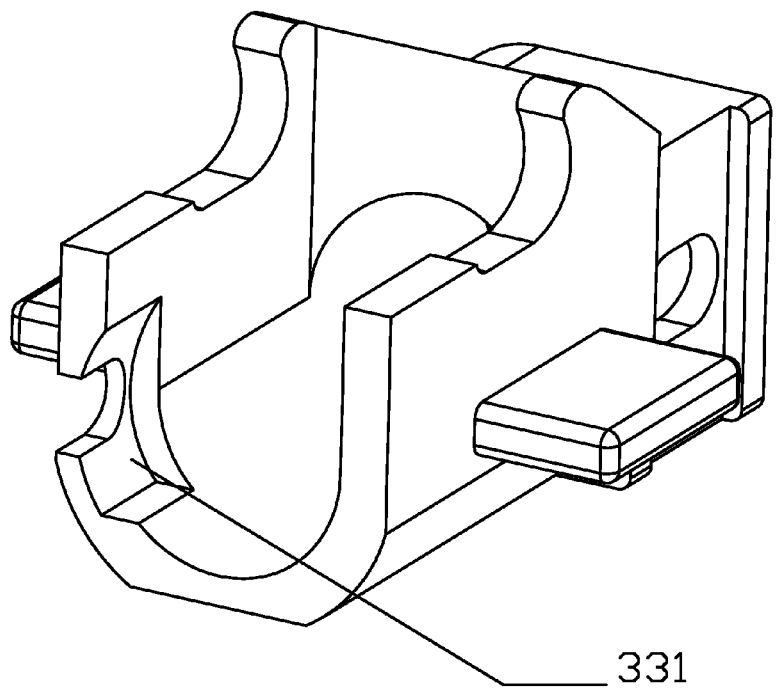
FIG. 5 is a structure diagram of a gap regulator of a stapler in accordance with one embodiment of the invention.

As shown in FIG. 1, a surgical stapler comprising a safety apparatus comprises: a fixed handle 1, a safety apparatus 2, a transmission assembly 3, a propulsion assembly 4, and a trigger handle 5. The safety apparatus 2 is fixed on the propulsion assembly 4 comprising an ejector sleeve 41 and contacts with a surface of the transmission assembly 3.

As shown in FIGS. 2-5, the transmission assembly 3 comprises a screw rod 31, a positioning connecting rod 32, and a gap regulator 33. The positioning connecting rod 32 comprises a chute 321. The positioning connecting rod 32 is in slide connection with the screw rod 31 via a first pin 34. The positioning connecting rod 32 is in flexible connection with the gap regulator 33 via a second pin 35 and an extension spring 36.

The positioning connecting rod 32 is provided with the chute 321, a positioning boss 322, and a groove 323. The screw rod 31 is provided with a boss 311 of a certain height. The gap regulator 33 is provided with a second limit slot 331 for matching with the positioning boss 322 of the positioning connecting rod 32. To make sure that the closing and opening of the safety apparatus 2 is synchronous with a transmission gap of the screw rod 31, the positioning connecting rod 32 and the screw rod 31 are in gap fit. Besides, the groove 323 of the positioning connecting rod 32 has a depth of smaller than a height of the boss 311 of the screw rod 31. The second pin 35 is designed to ensure the positioning connecting rod 32 and the screw rod 31 in fixed connection, and when the second pin 35 is fastened, the positioning connecting rod 32 and the screw rod 31 are in slide fit. The second pin 35 comprises a supporting plate having a height larger than a width of a fixed slot of the second pin 35 disposed on the screw rod 31.

Besides, the positioning boss disposed on the positioning connecting rod and the second limit slot disposed on the gap regulator make sure that both the positioning connecting rod and the screw rod cooperate with the gap regulator, the positioning connecting rod is in transmission connection with the safety apparatus, and the positioning connecting rod and the gap regulator are tightly connected as a whole by the extension spring, whereby the movement of the safety apparatus inside the surgical stapler is synchronous with the gap regulation of the screw rod.

Figure 6:
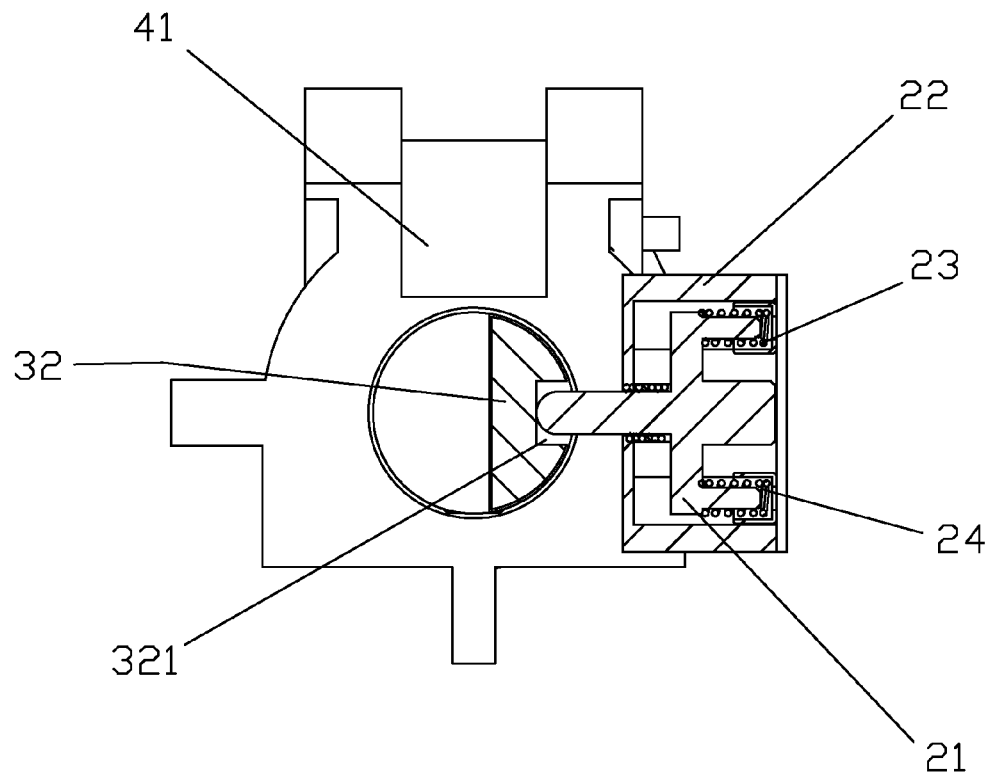
FIG. 6 is a cross sectional view of a side adjacent to an ejector sleeve of FIG. 2.
Figure 7:
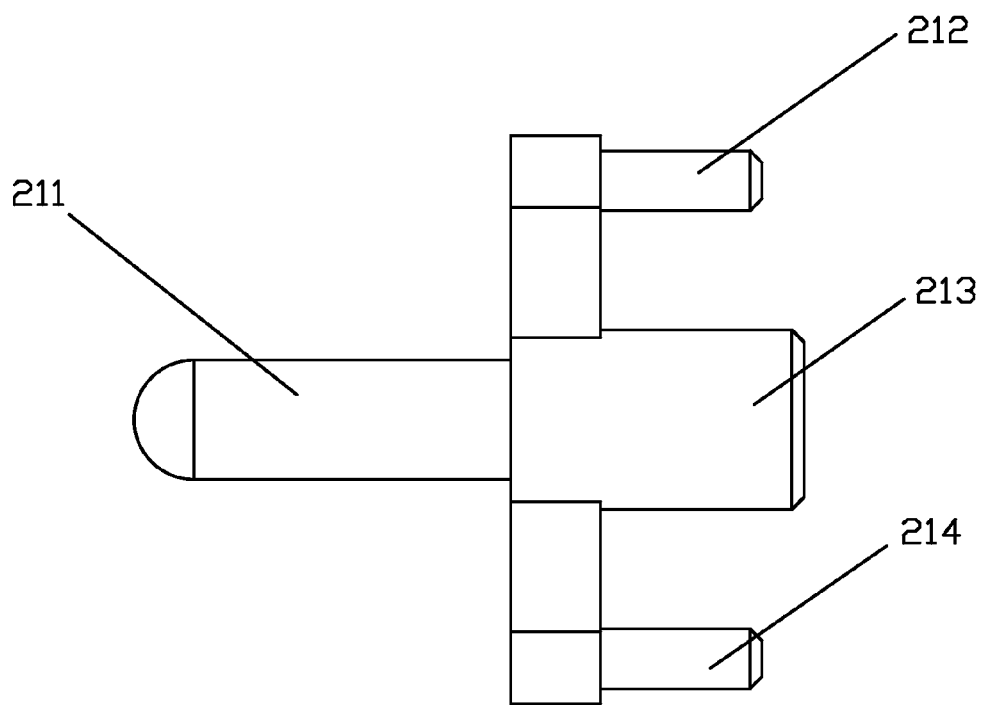
FIG. 7 is a structure diagram of a safety piece of a stapler in accordance with one embodiment of the invention.

As shown in FIGS. 6-7, the safety apparatus 2 comprises a safety piece 21 and a fixing block 22. The fixing block 22 is fixed on the ejector sleeve 41. The safety piece 21 is disposed inside the fixing block 22. At least one spring is disposed inside the fixing block 22 to ensure elasticity of the safety piece. An end face 211 of the safety piece 21 is capable of attaching to the chute 321 of the positioning connecting rod 32.

The safety device 2 is disposed on the ejector sleeve 41 of the propulsion assembly 4 and is locked inside a cavity of one side of the fixed handle 1 within a proper interval. Specifically, the safety apparatus 2 is fixed at one side of a proximal end of the ejector sleeve 41 of the propulsion assembly 4.

Preferably, the safety piece 21 is fixed inside the fixing block 22 via two or three compression springs.

A left side of the safety piece 21 comprises a convex strip 211, and a right side of the safety piece 21 comprises three convex strips 212, 213, and 214. An end face of the convex strip 211 of the left side is in elastic contact with the transmission assembly 3 via the compression springs 221 disposed inside the fixing block 22.

To ensure the convex strip 211 of the left side of the safety piece 21 always lean on the chute 321 of the positioning connecting rod 32 and in balance, two springs 23, 24 are symmetrically arranged in the right and the left of a central plane of the safety piece 21 whereby the safety piece 21 uniformly and stably presses on the chute 321 of the positioning connecting rod 32. With the axial movement of the positioning connecting rod 32, the safety piece 21 moves in a direction perpendicular to the axial direction along with the variation of concave and convex of the chute 321. When the safety piece 21 contacts with a surface (A) of the positioning connecting rod 32, the ejector sleeve 41 can be triggered; and when the safety piece 21 contacts with a surface (B), the ejector sleeve 41 cannot be triggered.

Preferably, an end face of the convex strip 211 of the left side of the safety piece 21 is designed to be a semi-sphere having a smooth surface so as to reduce friction between the safety piece 21 and the positioning connecting rod 32 during the movement of the screw rod 31. The upper convex strip 212 and the lower convex strip 214 of the right side of the safety piece 21 are provided with the compression springs 23, 24.

Figure 8:
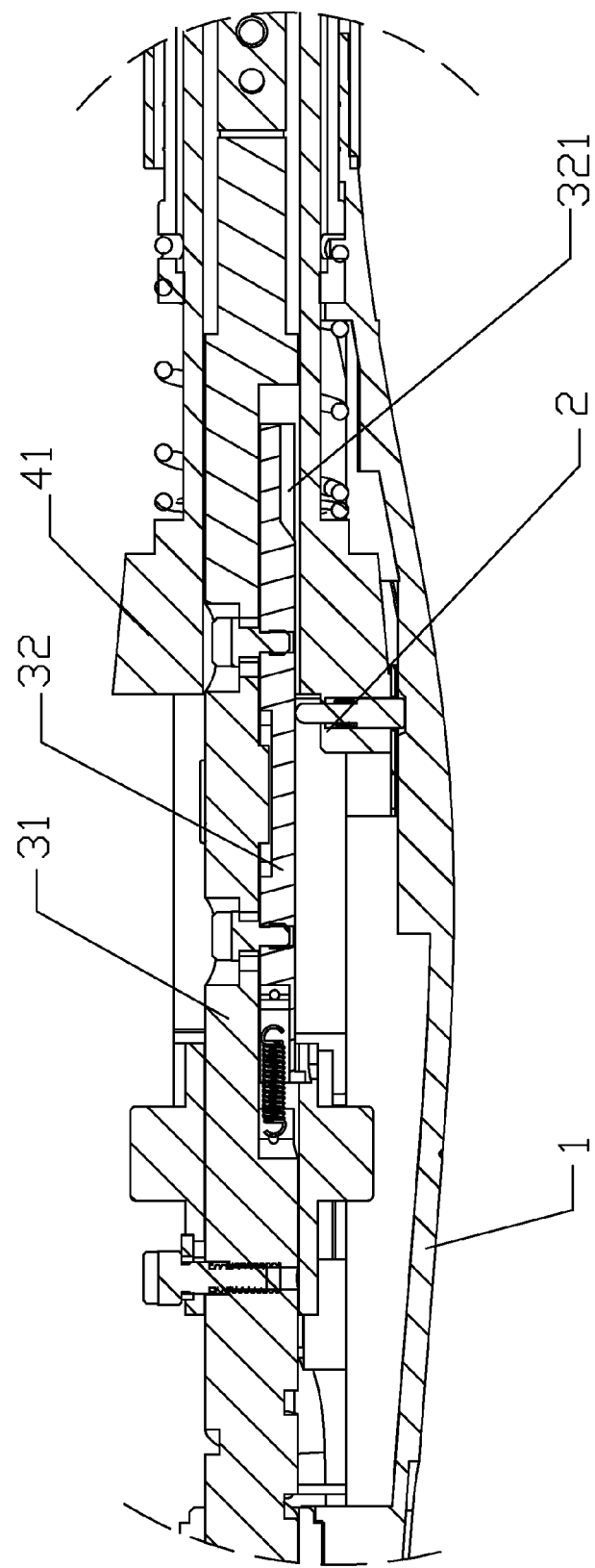
FIG. 8 is a cross sectional view of a locking device of a safety apparatus in accordance with one embodiment of the invention.

As shown in FIG. 8, the safety piece 21 is capable of moving in the direction perpendicular to the axial direction, and two node points exist on the motion tack of the safety piece 21. At a first node point 1, the ejector sleeve 41 is locked by the casing of the fixed handle 1, the ejector sleeve 41 cannot move in relation to the fixed handle 1, the surgical stapler cannot be triggered, and the safety device 2 is in an open state. At a second node point 2, the ejector sleeve 41 is separated from the casing of the fixed handle 1, the ejector sleeve 41 can move in relation to the casing of the fixed handle 1, the surgical stapler can be triggered, and the safety device is in a closed state.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A surgical stapler, comprising:
   a) a stapler part;
   b) a fixed handle;
   c) a safety apparatus, the safety apparatus comprising a safety piece and a fixing block having a cavity;
   d) a transmission assembly;
   e) a propulsion assembly, the propulsion assembly comprising an ejector sleeve; and
   f) a trigger handle;
   wherein:
   the safety apparatus is fixed on the propulsion assembly and contacts with the transmission assembly;
   the safety piece is disposed inside the cavity;
   at least one spring is disposed inside the cavity and the safety piece is inserted in the at least one spring whereby the safety piece is axially movable against the at least one spring;
   the transmission assembly comprises: a screw rod, a positioning connecting rod, and a gap regulator;
   the positioning connecting rod comprises a chute;
   the positioning connecting rod is in slide connection with the screw rod via a first pin; and
   the positioning connecting rod is in flexible connection with the gap regulator via a second pin and an extension spring.

2. The surgical stapler of claim 1, wherein an end face of the safety piece is adapted to contact with the chute of the positioning connecting rod.

3. The surgical stapler of claim 1, wherein a limit slot is disposed at one side of an inner cavity of a casing of the fixed handle.

4. The surgical stapler of claim 1, wherein an end of the safety piece contacting with the chute of the positioning connecting rod comprises an arc-shaped head.

5. A surgical stapler, comprising:
a) a stapler part;
b) a fixed handle;
c) a safety apparatus, the safety apparatus comprising a safety piece and a fixing block having a cavity;
d) a transmission assembly;
e) a propulsion assembly, the propulsion assembly comprising an ejector sleeve; and
f) a trigger handle;
wherein:
the safety apparatus is fixed on the propulsion assembly and contacts with the transmission assembly; and
the safety piece is disposed inside the cavity via two or three compression springs.

6. The surgical stapler of claim 1, wherein the screw rod comprises a boss; and the positioning connecting rod comprises a groove having a depth smaller than a height of the boss.

7. The surgical stapler of claim 1, wherein the positioning connecting rod comprises a positioning boss.

8. The surgical stapler of claim 1, wherein a limit slot is disposed on the gap regulator for matching with a positioning boss of the positioning connecting rod.

\* \* \* \* \*